United States Patent [19]

Benjamin

[11] 4,260,821

[45] Apr. 7, 1981

[54] MINIMIZING POLYMERIZATION DURING RECOVERY OF METHACRYLIC ACID

[75] Inventor: Bruce W. Benjamin, Fair Lawn, N.J.

[73] Assignee: Halcon Research and Development Corp., New York, N.Y.

[21] Appl. No.: 20,562

[22] Filed: Mar. 15, 1979

[51] Int. Cl.³ .................. B07D 3/34; C07C 15/235
[52] U.S. Cl. .......................... 562/532; 203/8; 203/49; 203/DIG. 21; 562/535; 562/600
[58] Field of Search ............... 562/600; 203/8, 9, 38, 203/49, DIG. 21

[56] References Cited

U.S. PATENT DOCUMENTS

| | | | |
|---|---|---|---|
| 2,143,941 | 1/1939 | Crawford . | |
| 2,373,464 | 4/1945 | Dittmar . | |
| 2,399,340 | 4/1946 | Franz | 203/9 |
| 3,666,794 | 5/1972 | Otsuki et al. | 562/600 |
| 3,674,651 | 7/1972 | Otsuki et al. | 203/8 |
| 3,761,516 | 9/1973 | Khoobiar | 562/534 |
| 3,794,567 | 2/1974 | Otsuki et al. | 203/8 |
| 3,816,267 | 6/1974 | Chuang | 203/8 |
| 3,838,019 | 9/1974 | Schwerdtel et al. | 203/49 |
| 3,855,075 | 12/1974 | Nachtigall | 203/49 |
| 4,010,082 | 3/1977 | Nemec et al. | 203/8 |
| 4,021,310 | 5/1977 | Shimizu et al. | 203/49 |
| 4,061,545 | 12/1977 | Watson | 203/49 |
| 4,087,382 | 5/1978 | Khoobiar | 252/455 R |
| 4,092,132 | 5/1978 | Leacock | 55/48 |
| 4,142,058 | 2/1979 | Matsumura et al. | 562/600 |

FOREIGN PATENT DOCUMENTS 7402808 12/1975 Brazil .

OTHER PUBLICATIONS

Mayo et al.: Oxidation of Methacrylic Esters, vol. 80, May 20, 1958, pp. 2493-2496.
Caldwell et al.: Inhib. of Oxid. and Polymeriz. of Methylmethacrylate by Phenols in the Presence of Air, Aug. 1962, pp. 2878-2886.
Boguslavskaya: Comparative Evaluation of Inhibiting Activity of Various Cmpds. with Respect to Acrylic and Methacrylic Monomers.
Doak et al.: Antioxidants, pp. 588-604, vol. 2.
Inhibition & Retardation: vol. 7.
Free-Radicate Polymerization: pp. 388-391.

*Primary Examiner*—Wilbur L. Bascomb, Jr.
*Attorney, Agent, or Firm*—William C. Long; David Dick; Harold N. Wells

[57] ABSTRACT

The presence of solid polymer in distillation columns and their associated reboilers used for the recovery of methacrylic and acetic acids produced by the oxidation of methacrolein may be minimized by the use of inhibitors and introduction of molecular oxygen at a rate above a predetermined threshold value, which is a function of the operating temperature of the equipment. For a given temperature, the amount of solids has been found to be greatly increased below the threshold value of oxygen, while above the threshold value, the rate of appearance of solids has been found to be minimized and further increases in oxygen rate have only a minimal effect. At a typical operation temperature of 120° C., the threshold value of about 0.1 SLH $O_2$/100 gm of liquid. A gas containing a relatively high concentration of oxygen is preferred.

2 Claims, 2 Drawing Figures

MINIMIZING POLYMERIZATION DURING RECOVERY OF METHACRYLIC ACID

PRIOR ART

This invention relates generally to minimizing the appearance of solids during the recovery of methacrylic acid formed by the vapor phase oxidation of methacrolein. Such solids can create serious fouling and/or plugging of distillation facilities. A process for the recovery of methacrylic acid by quenching the oxidation reactor effluent, followed by solvent extraction has been disclosed in another U.S. patent application. The solvents used in the extraction step were found to be critical to the minimizing of fouling and/or plugging which can seriously impair the subsequent separation of methacrylic acid and acetic acid by distillation from reaction by-products and unreacted methacrolein.

It has been long recognized that inhibitors are generally necessary in order to prevent polymerization of methacrylic acid or its related ester, methyl methacrylate. For example, in U.S. Pat. No. 2,143,941 Crawford mentions that hydroquinone and other materials were known inhibitors for the polymerization of unsaturated aliphatic carboxylic acids and their esters and derivatives. His invention related to the use of anhydrous metal halides to obtain improved results compared to those obtained with hydroquinone.

In view of the commercial importance of methacrylic acid and methyl methacrylate and related unsaturated organic compounds, considerable attention has been paid to the mechanism of polymerization and the effect of inhibitors, including their interaction with oxygen. A number of scientific publications have discussed the polymerization of methacrylic acid and methacrylates, for example, Mayo and Miller, *Journal of the American Chemical Society*, Vol. 80, page 2493 (1958), Caldwell and Ihrig, *Journal of the American Chemical Society*, Vol. 84, page 2878 (1962), and Boguslavskaya, Khim. Prom., Vol. 43 (10), page 749 (1967). In addition, reference may be made to general articles in the *Encyclopedia of Polymer Science and Technology*, Interscience Publishers, 1965, under the subjects Antioxidants, Inhibitors and Retardation, and Free Radical Polymerization.

Hydroquinone and similar inhibitors have been often classed as antioxidants and have been found not to be as useful as polymerization inhibitors in the absence of oxygen (see U.S. Pat. No. 4,010,082, Nemec, et al.). On the other hand, oxygen itself has been considered by some investigators to be an inhibitor, although it is normally used in conjunction with inhibitors such as hydroquinone. In this regard, reference may be made to U.S. Pat. No. 2,373,464 where, in a process for preparation of an ester of methacrylic acid, oxygen is added in the presence of hydroquinone or pyrogallol. The recommended amount of oxygen is from 0.01 to 10 ft$^3$ air/pound of monomer (0.012 liters oxygen/100 gms to 12 l $O_2$/100 gms) in continuous processing or from 0.001 to 10 ft$^3$ air/pound of monomer (0.0012 liters oxygen/100 gms to 12 liters $O_2$/100 gms) batch systems.

The means by which hydroquinone and other phenolic inhibitors may function as polymerization inhibitors has been extensively studied. Some investigators have suggested that hydroquinone is converted to benzoquinone or semi hydroquinone, which operates to terminate the growing polymer chain. Chuang in U.S. Pat. No. 3,816,267, disclosed that oxidation of hydroquinone to benzoquinone by contact with air gives erratic results and that by using a mixture of the quinone and the enol derivative provides improved and more predictable inhibition of the polymerization of acrylates.

It has been suggested also that oxygen may combine with free radicals in order to form peroxides and thereby slowing the formation of polymers. If oxygen is not replenished, it is consumed by reaction with monomers until it has been exhausted and thereafter the normal polymerization mechanism controls. In any event, the art teaches that there is an interaction between hydroquinone (and similar inhibitors) and oxygen by which they minimize the polymerization of methacrylic acid or methyl methacrylate.

A number of inhibitors have been suggested for use in the inhibition of polymerization. One disclosure of interest is Brazilian patent application No. 74-02808 by Ikeda, et al., of the Mitsubishi Rayon Company, in which improved results were shown for the use of p-phenylene diamine and its derivatives as compared to the use of hydroquinone and other familiar inhibitors. Ikeda disclosed the use of 0.01 vol % air or oxygen based upon the amount of vapor in the column, which could be introduced into the vapor space or bubbled into the liquid at the bottom of the column.

In the commercial scale preparation of methacrylic acid by oxidation of methacrolein, it has been found that by the proper selection of the solvents used to extract methacrylic acid and acetic acid, it is possible to significantly reduce the amount of polymer and other high-boiling materials which appear as solids in subsequent distillations for the recovery of methacrylic acid and acetic acid. However, a further improvement was desired in order to minimize losses of methacrylic acid and the operating difficulties which follow from the appearance of solids in the distillation facilities used to recover methacrylic acid and acetic acid. The present invention to be described hereinafter is concerned with the optimization of the use of inhibitors and oxygen for the purpose of minimizing such difficulties.

SUMMARY OF THE INVENTION

The appearance of polymers and/or other high-boiling materials as solids during the recovery of methacrylic acid produced by oxidation of methacrolein can be minimized by the use of known inhibitors such as hydroquinone and the like, and the introduction of molecular $O_2$, in the form of air or enriched air, at a rate above a threshold value, defined as the amount of oxygen above which no significant reduction of the rate of appearance of solids occurs. The threshold value is primarily affected by the temperature of the boiling liquids where solid polymers are expected to appear. At an operating temperature of about 120° C. the threshold value is at about 0.1 SLH $O_2$/100 gms of liquid. Amounts of oxygen above threshold value may be used but, by definition, are not necessary, while reducing the oxygen rate below the threshold value results in the appearance of sharply increased amounts of solids. Contacting of gas bubbles containing oxygen with the boiling liquids will affect the ability to operate satisfactorily with threshold quantity of oxygen. Consequently, it is preferred that a gas containing a relatively high concentration of oxygen be used.

DESCRIPTION OF THE PREFERRED EMBODIMENTS

Minimizing the fouling and/or plugging by polymers and other high-boiling materials during the recovery of methacrylic acid is important in the commercialization of a process for producing methacrylic acid. Since the nature of the troublesome fouling compounds will be determined by the process in which the methacrylic acid is made, the following brief description outlines the two-stage process by which isobutylene and/or tertiary butyl alcohol are converted to methacrylic acid and which provides the feed stock to the recovery process in which the invention has particular application.

The feed material, either/or isobutylene and tertiary butyl alcohol, are introduced along with molecular oxygen, into a first oxidation stage for conversion to methacrolein in the presence of a suitable catalyst, such as that disclosed in U.S. Pat. No. 4,087,382. Substantial quantities of water vapor and inert gases typically are present in the reactor, but they are not necessarily added as such. Nitrogen may enter with the oxygen supply, and if that is the case, nitrogen must be purged to maintain the desired amount in the oxidation reaction. Although water is produced in the oxidation reaction, still larger amounts are needed, and if not added directly as steam, it may be added indirectly by adjusting of the water content of the recycled reaction gas stream, after the product methacrolein has been removed. The reaction typically is carried out at a temperature in the range of about 330°-500° C. and at a pressure of up to about 14 kg/cm$^2$ gauge. Since the reaction is highly exothermic, the catalyst is often placed inside small diameter tubes and the heat of reaction removed by circulating a molten salt on the outside of the tubes.

After separation of methacrolein from the effluent of the first-stage reactor by water scrubbing or other means such as absorption in acetic acid, as shown in U.S. Pat. No. 4,092,132, the remaining gases may be recycled to the first-stage reactor to convert any unreacted isobutylene and to provide nitrogen and water vapor to the reaction mixture as mentioned above.

After recovery, the methacrolein is fed to the second stage where it is oxidized by molecular oxygen to methacrylic acid in the presence of substantial amounts of water vapor and nitrogen at temperatures typically in the range of 270°-450° C. and at pressures up to about 7 kg/cm$^2$ gauge, over a mixed base metal oxide catalyst, which will ordinarily differ from the composition of the first-stage catalyst. The comments made previously with regard to the direct introduction of steam and inerts apply to this second stage also.

Figure 1:
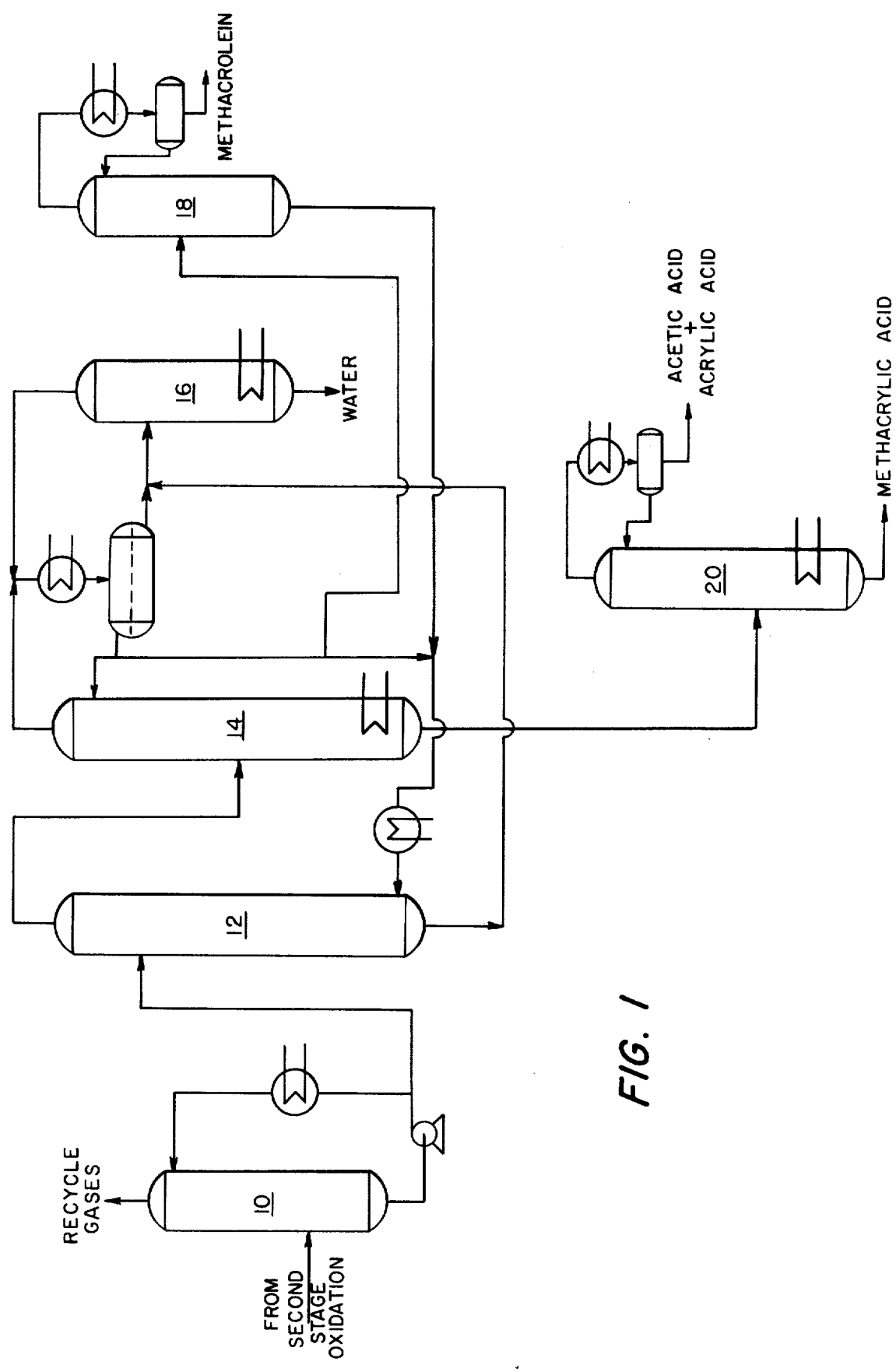
FIG. 1 shows a schematic flow sheet of a recovery process for methacrylic and acetic acids.

Methacrylic acid is recovered from the second oxidation stage effluent and purified as shown in FIG. 1. Acetic acid may be recovered along with the methacrylic acid and separated as a useful by-product by the process. The recovery process to which the present invention is particularly applicable begins with the cooling and condensation of reactor effluent gases in quench tower 10. Residual gases are separated and recycled to the second-stage reactor. Extraction of crude methacrylic acid with a suitable solvent is carried out in column 12. Purification of the acid includes separation of the solvent from crude methacrylic acid (including acetic acid) by distillation in column 14 with recirculation of the solvent to the extraction step. Crude methacrylic acid is separated into a pure methacrylic acid product and a by-product stream containing acetic acid and acrylic acid as the principal constituents in column 20. Purification of the acetic acid may be carried out in subsequent distillations, not shown.

Although most of the water in the reactor effluent is rejected during the solvent extraction, a certain amount of water is carried into the solvent recovery column 14 and is separated from the solvent in the overhead facilities. The combined water from the extraction column 12 and solvent recovery column 14 is overhead is stripped of dissolved solvent in column 16 and rejected, while the recovered solvent is returned to the solvent recovery column (14) overhead equipment. A portion of the unreacted methacrolein tends to accumulate in the solvent and recovery by distillation of a slip stream of solvent is generally economically justified. Such a column is shown as 18 in FIG. 1.

It has been found that fouling and/or plugging of the distillation columns, and particularly their reboilers, is a common problem when processing solvent rich in methacrylic acid and acetic acid. The nature of the fouling materials is not fully known, however, it has been found that by use of conventional inhibitors, particularly hydroquinone, fouling may be greatly reduced, but only when used in conjunction with oxygen injection at a rate above a predetermined threshold value which has been found necessary to prevent serious fouling of the equipment.

Inhibitors which may be used in conjunction with the present invention include those known in the art such as aromatic phenols, aromatic amines, and quinones. Hydroquinone and the commercially available A-30, 2,4 dimethyl 6 t-butyl phenol available from DuPont, along with Topanol A, 2,4 dimethyl 6 t-butyl phenol available from ICI United States, Inc., have been found to be useful. The amounts of inhibitor(s) will be generally similar to those known in the art, typically between 100 and 1000 ppm (wt).

It is believed that the fouling is related to the higher boiling components found in the crude methacrylic acid, as shown by the following experimental results obtained with a crude methacrylic acid produced by the two-stage oxidation process previously described and containing 20.5 mol % methacrylic acid, 4.1 mol %, acetic acid, 0.2 mol % acrylic acid, 1.4 mol % methacrolein, and containing 500-1000 ppm of hydroquinone as an inhibitor. A portion of the crude methacrylic acid was flashed under vacuum to provide an overhead liquid containing 95% of the crude acid, and a bottoms liquid containing 5% of the crude acid which was diluted with sufficient pure methacrylic acid, acetic acid, and acrylic acid to approximate the original crude acid composition. Samples of the crude acid, the flashed liquid, and the reconstituted flash bottoms were each held for one hour at 120° C., while 0.07 SLH O$_2$/100 gm (Std. liters per hour oxygen/100 gms of crude acid) was bubbled through the liquid in the form of 5% oxygen in nitrogen. Solids which were formed during the holding period were measured after filtration and vacuum drying.

TABLE I

| Test Liquid | % Solids |
|---|---|
| Crude methacrylic acid | 4.6 |
| 95% crude methacrylic acid (overhead of flash) | 0.03 |

TABLE I-continued

| Test Liquid | % Solids |
| --- | --- |
| 5% crude methacrylic acid (bottoms of flash) + pure acids | 5.2 |

The above results show that the highest boiling fraction of the crude methacrylic acid is the source of essentially all of the solids. The pure acids used to dilute the 5% portion of the crude acids are known to produce very small amounts of solids when heated in the presence of inhibitor and oxygen as used in the above experiment and thus would not have significantly affected the results. It is concluded then that the process for producing methacrylic acid by two-stage oxidation of isobutylene and/or tertiary butyl alcohol forms by-products which result in solids formation and which are primarily found in the heaviest 5% of the crude methacrylic acid. The present invention is directed toward the minimizing of the fouling by such solids of the distillation columns used to recover methacrylic acid and acetic acid.

Tests have indicated that for a given liquid there exists a minimum threshold rate of oxygen which must be used in order to minimize solids formation even in the presence of inhibitors. This threshold is a function of temperature where the gas and liquid are well mixed. However, it appears that the amount of oxygen actually used is affected by the effectiveness of gas-liquid contacting. Use of gases containing relatively high concentrations of oxygen (say 50 vol %) are preferred to offset possible mixing deficiencies, although other process advantages are obtained by limiting the amount of extraneous gases introduced. At a typical operating temperature of about 120° C., it has been found that the threshold value is about 0.1 SLH/100 gm liquid.

While the underlying principles governing the introduction of oxygen to minimize the formation of solids are not entirely clear, it is believed that the discovery that the threshold amount of oxygen required is related to the amount of liquid present, rather than the vapor, is important. The prior art often discloses the concept of relating the amount of oxygen used to the amount of vapor present and one skilled in the art might suppose that contact of the oxygen with the liquid present was unimportant. However, as the present inventor's data show, a correlation may be made between the amount of oxygen passed through a unit amount of liquid and the amount of solids formed. Since it has been observed that most of the oxygen passes through the liquid unreacted, it might be speculated that a critical concentration of oxygen in the gas is necessary to supply a small amount of oxygen to the liquid. This explanation would be consistant with the disclosures of the prior art. However, the data to be presented below indicate that, to the contrary, there is a relationship between the formation of fouling solids and the quantity of oxygen (and independent of concentration) passed through the liquid for each unit of liquid.

This finding may be interpreted as the consequence of a diffusion limitation on the supply of oxygen to the liquid if it is assumed that the amount of oxygen needed to suppress polymerization for a given amount of liquid is constant for a particular temperature, since the reaction being suppressed will be dependent upon temperature. It has been shown both theoretically (see Levich, *Physio-Chemical Hydrodynamics*, Prentice Hall, 1962) and experimentally (see *Chemical Engineer's Handbook*, McGraw Hill, 4th Ed. 1963) that the rate of diffusion of oxygen is directly proportional to its concentration in the gas bubbles and is a function of other factors such as, the size of the gas bubbles and the degree of agitation. If all other factors are constant, the quantity of oxygen absorbed into a liquid from a single bubble is dependent upon the concentration of oxygen in the bubble, and therefore the total amount of oxygen absorbed into liquid should be dependent upon the total number of bubbles in the system, which is determined by the total amount of oxygen sparged to the given liquid volume. Since the degree of agitation and other factors affect the bubble size distribution, then it can be seen that the total oxygen diffusing from the bubbles of sparge gas into the liquid will not be solely a function of the total oxygen sparged, although the data suggest that it is the major factor in the systems studied.

The data of Table II does not support a correlation of fouling with the oxygen concentration of the gas. They were taken in a batch system in which a fixed amount of crude methacrylic acid containing 85 wt. % methacrylic acid, 1? wt. % acetic acid, 1 wt %. acrylic acid was held at a temperature of about 120° C. (a temperature just below the boiling point) while an oxygen containing nitrogen gas was passed through the liquid. The rate of gas flow and the oxygen content (5% or less) were the only factors varied. The solids formed were filtered from the liquid and weighed. The liquid contained about 3000 ppm of hydroquinone and about 1000 ppm of Topanol A.

TABLE II

| SLH $O_2$/ 100 gm liquid | Mol % $O_2$ in vapor | % Solids |
| --- | --- | --- |
| 0.125 | 3.8 | 0.03 |
| 0.125 | 1.5 | 0.05 |
| 0.125 | 1.5 | 0.03 |
| 0.11 | 0.2 | 0.30 |
| 0.1 | 3.8 | 0.04 |
| 0.1 | 3.8 | 0.03 |
| 0.1 | 3.8 | 0.08 |
| 0.1 | 3.8 | 0.03 |
| 0.07 | 3.8 | 5.30 |
| 0.07 | 3.8 | 4.32 |
| 0.06 | 0.2 | 5.33 |
| 0.05 | 1.5 | 4.90 |

Several observations may be made, based on this experiment. First, the threshold value for this system is about 0.1 SLH $O_2$/100 gm of liquid; below this value the formation of solids is very rapid. Second, the concentration of oxygen in the gas has no relation to the amount of solids formed. Note that both a high and a low solids make were obtained at the same oxygen concentrations. Within both regimes the variation of oxygen concentration, although quite large, clearly was not correlated with the amount of solids formed. Finally, under the conditions of this test the relationship between oxygen rate and the formation of solids was not influenced by heat transfer effects, such as high surface temperatures, or mass transfer effects such as the presence of vaporizing acids which would be expected to obscure a test carried out with a boiling liquid.

A similar experiment was carried out in a batch system in which crude methacrylic acid having approximately the same composition as in the previous experiment was boiled. Such a system should approximate the situation encountered in distillation columns more accurately than the previously described experiment. However, a significant scatter in the rate of solids formation was found, possibly because the mass transfer characteristics of a boiling system cannot be easily standardized. The liquid velocity, mixing of vaporized liquid with sparge bubbles, counterdiffusion of vapor into the bubbles of sparge gas, localized heating effects, and residence time phenomena can all contribute to non-reproducibility of results. Despite these difficulties, a threshold value can be identified which, as before, is related to the total amount of oxygen passed through a unit volume of liquid.

Figure 2:
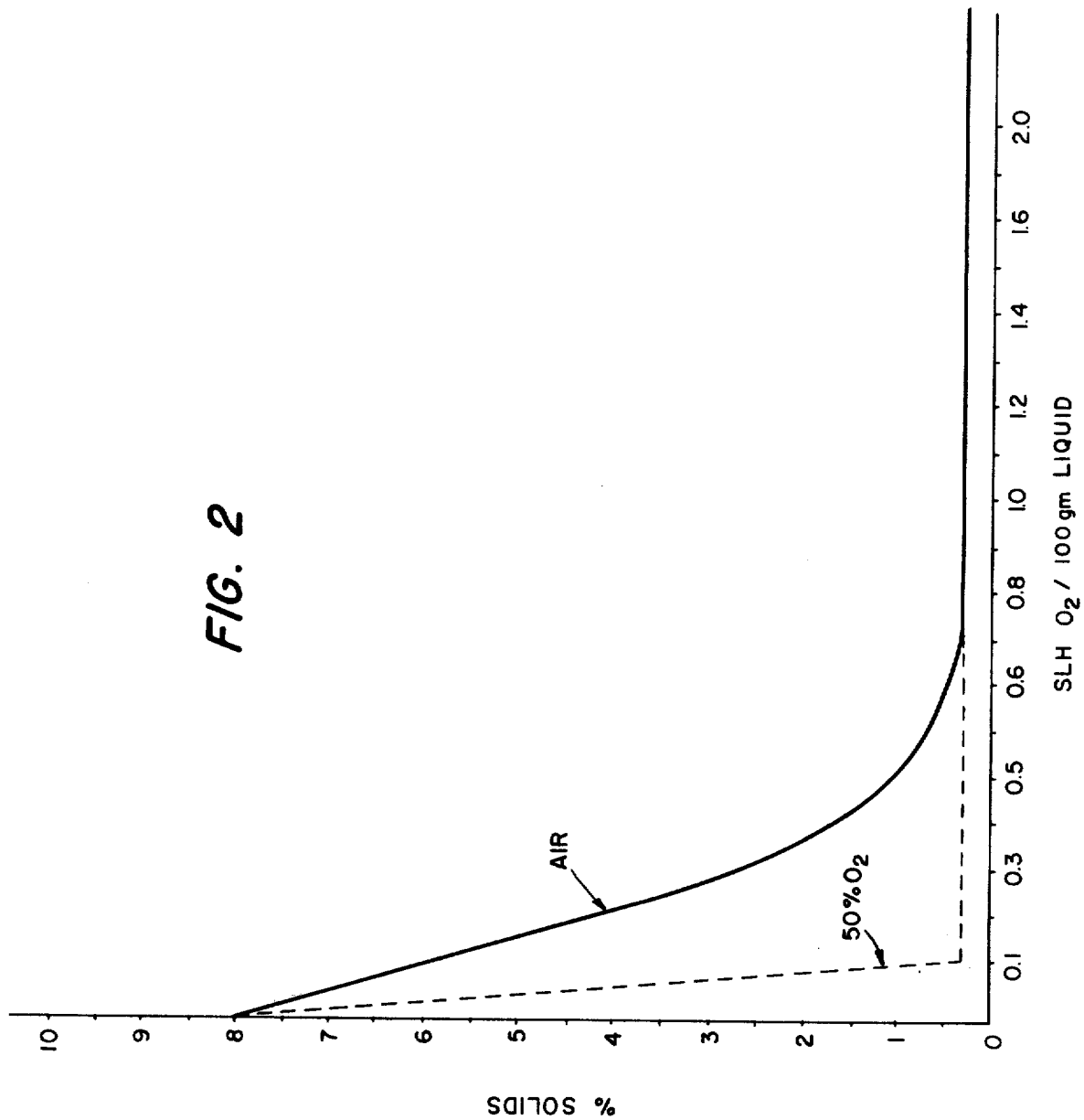
FIG. 2 graphically presents the relationship between oxygen concentration and rate and solids formation.

A series of experiments were carried out in which 60 grams of a liquid charge of crude methacrylic acid was heated and held at about 110° C. under a pressure of 200–220 mm Hg absolute for a period of one hour, while oxygen containing gases were bubbled through the liquid. After the holding period was completed, the liquid was cooled quickly (about 3–6 minutes) and the amount of solids determined by after filtration and vacuum drying. The crude methacrylic acid contained 80 mol % methacrylic acid, 12 mol % acetic acid, 0.5 mol % acrylic acid, and 7.5% other materials. An inhibitor designated as AO-30, obtained from DuPont was used at the level of 500 ppm. In order to determine the necessary amount of oxygen to minimize the solids produced by heating, the rate of oxygen was varied and the results plotted, as shown in FIG. 2. In this case, the concentration of oxygen in the sparged gas had a marked effect on the amount of solids produced near the threshold value, even though the absolute amount of oxygen passing through the liquid remained the same. The raw data show that a gas containing 50 mol % $O_2$ is preferred since it appears to provide more consistent results, that is, it would appear that the amount of oxygen required could be predicted more accurately than would appear possible with the lower concentrations of oxygen in the sparged gas. Based on the curves of FIG. 2, an oxygen rate of about 0.1 SLH/100 gms of liquid should be used with a gas containing 50% $O_2$. However, when air is sparged the threshold appears to be about 0.6 SLH/100 gms of liquid. However, the actual data are scattered and some indicate the threshold could be 0.1 SLH/100 gms as would be theoretically expected. It is believed that mass transfer parameters, such as the sparge gas velocity and the bubble size distribution, were less favorable when air was sparged in the test equipment used. It is expected that the air threshold would be about 0.1 SLH $O_2$/100 gms of liquid if mass transfer characteristics were improved. Lower concentrations of oxygen in inert gases may be used, although experience has indicated that still less favorable mass transfer conditions may be present, and thus higher concentrations of oxygen in the sparged gas are preferred. Also use of gases having low oxygen content will add to the operating costs in order to accomodate the increased quantity of inert gases.

The foregoing results based on batch experiments have been confirmed in continuous runs of the methacrylic acid recovery process. Tests have indicated that an 50% $O_2$–50% $N_2$ injection rate of 0.2 SLH $O_2$/100 gms liquid in a tower reboiler is adequate to maintain a low solids concentration, provided that at least about 100–1000 ppm hydroquinone is present.

What is claimed is:

1. In the process for preparation of methacrylic acid by the vapor phase oxidation of methacrolein with molecular oxygen in the presence of a catalyst and the recovery of said methacrylic acid by quenching and condensing the effluent of said oxidation with crude methacrylic acid solution and extracting the methacrylic acid by a solvent and distilling said solvent from said crude methacrylic acid solution and purifying methacrylic acid from said crude solution, the improvement comprising carrying out said distilling and purifying of crude methacrylic acid in the presence of an effective amount of polymerization inhibitor and introducing molecular oxygen into liquid methacrylic acid-containing solutions at a rate expressed as SLH $O_2$/100 g of liquid above about 0.1.

2. The process of claim 1 wherein said molecular oxygen is introduced into said liquid solutions as a gas having a concentration of 50 mol % oxygen.

* * * * *